United States Patent [19]

Safadago

[11] Patent Number: 4,846,807
[45] Date of Patent: Jul. 11, 1989

[54] IV TUBE ANCHOR AND SHIELD

[76] Inventor: Gary J. Safadago, 9522—1st Northeast, Suite A4, Seattle, Wash. 98115

[21] Appl. No.: 163,173

[22] Filed: Feb. 26, 1988

Related U.S. Application Data

[63] Continuation of Ser. No. 858,134, Apr. 30, 1986, abandoned.

[51] Int. Cl.$^4$ ............................................. A61M 25/02
[52] U.S. Cl. ............................. 604/179; 128/DIG. 26
[58] Field of Search ..................... 604/174, 179, 180; 128/133, 132, DIG. 6

[56] References Cited

U.S. PATENT DOCUMENTS

| | | | |
|---|---|---|---|
| 2,449,882 | 9/1948 | Daniels ........................ | 128/DIG. 26 |
| 3,059,645 | 10/1962 | Hasbrouck et al. ................. | 604/179 |
| 3,900,026 | 8/1975 | Wagner ............................ | 604/174 X |
| 4,197,845 | 4/1980 | Browning ......................... | 128/153 X |
| 4,449,975 | 5/1984 | Perry ..................... | 604/179 |
| 4,516,968 | 5/1985 | Marshall et al. ..................... | 604/174 |
| 4,517,971 | 5/1985 | Sorbonne ......................... | 604/174 X |
| 4,574,298 | 3/1986 | Heitzman ............... | 128/DIG. 26 X |
| 4,582,508 | 4/1986 | Pavelka .............................. | 604/179 |

Primary Examiner—Stephen C. Pellegrino
Attorney, Agent, or Firm—Ward Brown; Robert W. Beach

[57] ABSTRACT

A continuous frame of resilient foam material is strapped to a patient with a central aperture of the frame surrounding the puncture area of an intravenous (IV) needle inserted into the patient. A separate dome with ventilation apertures is attachable over the central aperture of the frame to shield the needle. The IV tube is anchored to the frame at a plurality of different locations such that tension applied to the tube is not transmitted to the needle to dislodge it.

6 Claims, 3 Drawing Sheets

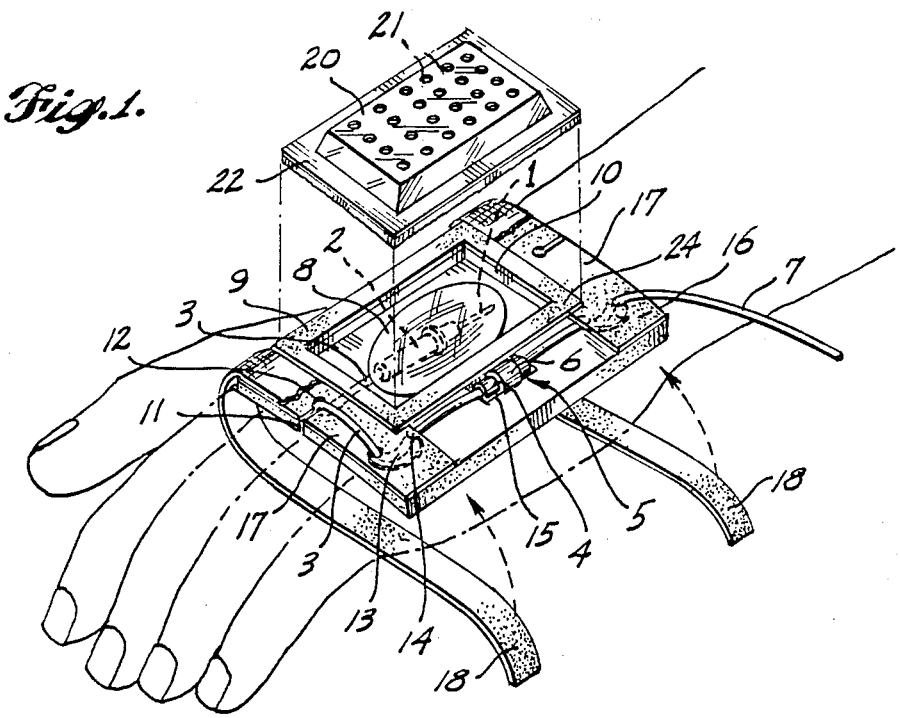
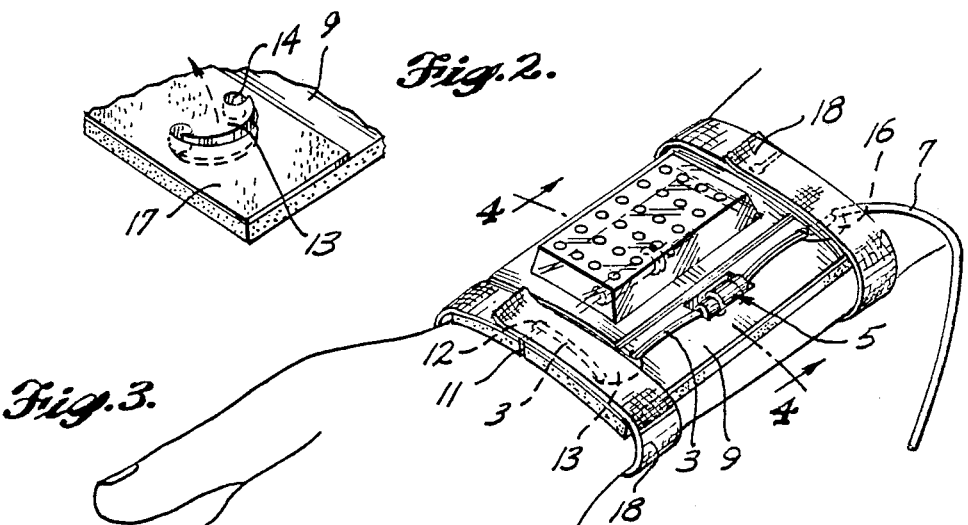
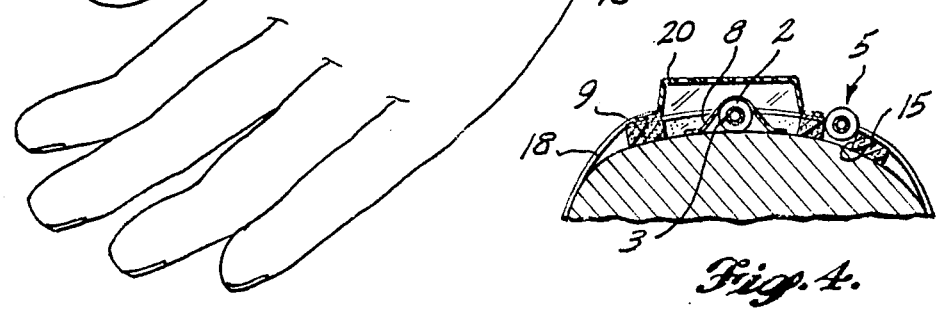
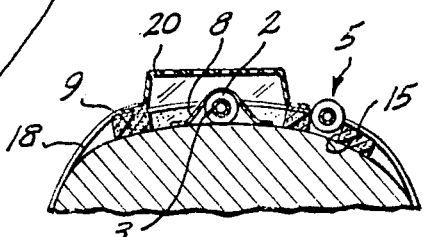

IV TUBE ANCHOR AND SHIELD

This is a continuation of copending application Ser. No. 858,143, filed on Apr. 30, 1986, now abandoned.

BACKGROUND OF THE INVENTION

1. Field of the Invention

The present invention relates to a device that can be strapped to the body over the location of insertion of an intravenous (IV) needle to shield the puncture area against contact and for anchoring the IV tube so that the needle will not be pulled out inadvertently.

2. Prior Art

It is known to apply a self-adhesive sheet, film or membrane over the area of insertion of an IV needle into the body, primarily for the purpose of keeping the area clean. The covering sheet does not substantially protect or anchor the needle or IV tube.

The rigid connector between an IV needle and its tube sometimes is covered by a small plastic pill cup which is taped to the body, but the cup does not offer substantial protection against dislodging the needle by tension exerted on the tube.

The problem of protecting the area of the body into which an IV needle has been inserted and anchoring the IV tube in such manner that dislodging it inadvertently is unlikely is of particular importance for children with an illness requiring frequent or prolonged hospitalization. Under current techniques, a child quickly develops a fear of the needle and goes to extremes in trying to protect it, yet may inadvertently dislodge the needle, sometimes while asleep. Consequently, the activity of the child can be affected adversely and, of course, the health of the child may be jeopardized if dislodgment of the needle is not detected for a substantial period. In addition, it can be extremely important that an IV needle remain inserted as intended if there are few or no remaining veins accessible without surgery.

SUMMARY OF THE INVENTION

The principal object of the present invention is to provide a device for shielding the area of the body into which an IV or other needle for introducing therapeutic liquid is inserted and for anchoring the IV tube closely adjacent to the point of insertion such that painful contact of an object with the IV needle is unlikely and tension applied to the IV tube will not be transmitted to the needle so as dislodge the needle.

An additional object is to provide such a device in simple, compact, inexpensive form, easy to use and reliable for shielding the IV needle and anchoring the IV tube for a long period even on infants or children.

In the preferred embodiment of the present invention, the foregoing object is accomplished by a continuous frame of resilient foam material with a central aperture of a size sufficient to surround the puncture area of the IV needle. A separate dome or shield with ventilation apertures is attachable over the central aperture of the frame. The IV tube is threaded through a slot and under tabs in the frame to a return bent, or, preferably, serpentine path, and is maintained in position by straps which also secure the frame and dome combination to the body.

BRIEF DESCRIPTION OF THE DRAWINGS

FIG. 1 is a diagrammatic top perspective of an IV tube anchor and shield in accordance with the present invention with some parts only partially assembled, illustrating application of the device to the back of the hand of a patient.

FIG. 2 is an enlarged, fragmentary, top perspective of a corner portion of the IV tube anchor and shield shown in FIG. 1.

FIG. 3 is a top perspective of the IV tube anchor and shield shown in FIG. 1, but with parts assembled, illustrating application of the device to the underside of the wrist of a patient; and FIG. 4 is a section along line 4—4 of FIG. 3.

DETAILED DESCRIPTION

Figure 5:
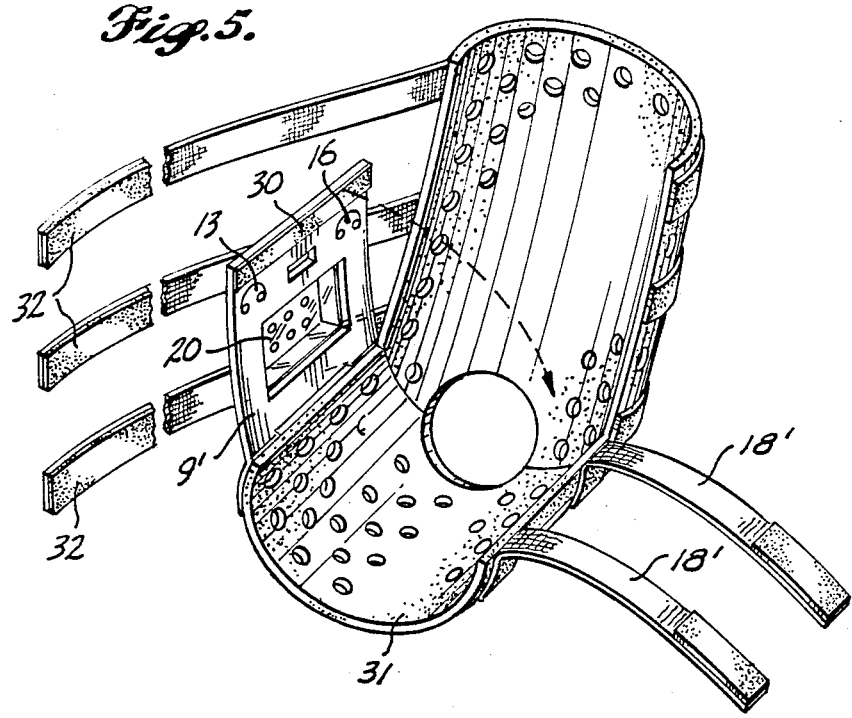
FIG. 5 is a top perspective of a slightly a slightly modified form of an IV tube anchor and shield in accordance with the present invention mounted on a larger cuff.

FIG. 1 illustrates a representative type of IV needle 1 and its immediately adjacent rigid needle and tube holder 2 with the usual narrow IV tube 3 that extends to the male component 4 of a joint 5. Such joint includes the female component 6 on the end of the usually larger IV tube 7 which extends to a metering device controlling the flow of therapeutic liquid from a bottle or other reservoir. The needle is inserted into a convenient vein which may be on the back of the hand as shown in FIG. 1. The rigid needle holder 2 and immediately adjacent area usually are covered by a thin sheet, film or membrane 8 which has a self-adhesive bottom surface and which is intended to keep the puncture area clean.

In accordance with the present invention, the area of insertion of the needle 1 and its holder 2 is surrounded by an anchor member or frame 9. The frame has a central aperture 10 fitted over the covering sheet 8. The short narrow section of IV tube 3 from the rigid holder and connector 2 to the joint 5 extends under an end of frame 9 and upward through a slot 11. The inner portion 12 of the slot can be slightly enlarged to snugly retain the tube in position without crimping or kinking it. Next, the tube section 3 is fitted under a flap or tab 13 in an adjacent corner portion of the frame. As seen in FIG. 2, the tab 13 can be bent upward so that the tube can be inserted under the tab so as to be lightly clamped between the the tab and the remainder of the frame. Preferably, the tab is integral with the remainder of the frame and is formed by a generally U-shaped cut or slit with enlarged circular portions 14 at the opposite ends for snugly receiving the tube without kinking or crimping it. The tab normally closes the opening of the frame defined by the slit.

The joint 5 joining the tube sections 3 and 7 can be fitted in a recess 15 in the frame, at the same side of the frame as the corner tab 13. The other corner portion of the frame at the same side has a flap or tab 16 identical to the tab 13 for receiving the tube section 7.

The opposite ends of the frame have strips of fastening material 17, preferably the hook type material of hook-and-pile fastenings. Straps 18 of the pile, loop or foam type fastening material which is complementary to the hook type fastening material can be looped around the hand and wrist for securing the frame in position. As best seen in FIGS. 3 and 4, preferably the straps extend directly over the tabs 13 and 16 to hold the tabs down and prevent the tubes 3 and 7 from escaping.

In assembled condition, the IV tube 3, 7 is turned at the frame slot 11, again at tab 13 and again at tab 16. Preferably the tube is return bent at least once and follows a serpentine path. The tube is anchored to the frame at two, preferably at least three, of the turns of such path, making it extremely unlikely that tension applied to the tube 7 will be conveyed to the tube section 3 adjacent to the rigid connector 2 so as to dislodge the needle.

In the preferred embodiment, the central aperture 10 of the frame 9 can be closed by a removable rigid dome or shield 20 having ventilation apertures 21. The dome can have a flat marginal flange portion 22 with one type of the complementary fastening material along the underside of the flange to mate with the other type of fastening material arranged in a circumferential strip 24 along the top margin of the frame aperture. With the shield in position, the puncture area is substantially enclosed.

In the preferred embodiment, the frame is somewhat resilient and flexible closed cell foam material of a thickness of about ¼ inch (0.63 cm) to about ½ inch (1.27 cm).

FIG. 3 illustrates the assembled frame, strap and dome construction as applied to the underside of patient's wrist. As seen in FIG. 4, if the frame is of a thickness less than the height of the rigid needle holder portion 2, the dome or shield 20 must have a concave underside allowing room for such holder and protecting the holder and needle from inadvertent contact.

Figure 6:
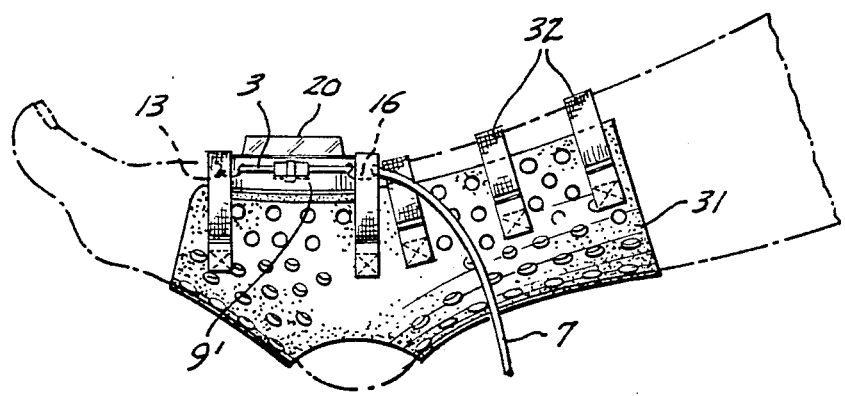
FIG. 6 is a side elevation showing such modified form and cuff applied to the foot of a patient.

The slightly modified frame 9' shown in FIG. 5 is identical to the frame shown in FIGS. 1 through 4 with the exception that strips 30 of one type of the hook-and-pile fastening material are secured to the underside of the frame 9' along its longitudinal side edges to adapt the frame for attachment over a cuff 31. The cuff is contoured to fit around the bottom of the foot and the back of the ankle portion of a patient as shown in FIG. 6 and can be secured in position by quick-coupling straps 32. The frame 9' is positioned over the top of the foot, between the opposite sides of the cuff, where there is a vein which can be used for intravenous introduction of liquid. Additional straps 18' extend over the opposite ends of the frame to retain its tabs 13 and 16 in position after the IV tube sections 3 and 7 have been fitted under them. Consequently, the frame is maintained securely in position over the top of the foot to protect the IV needle inserted in that location which is common for hospitalized children.

Figure 7:
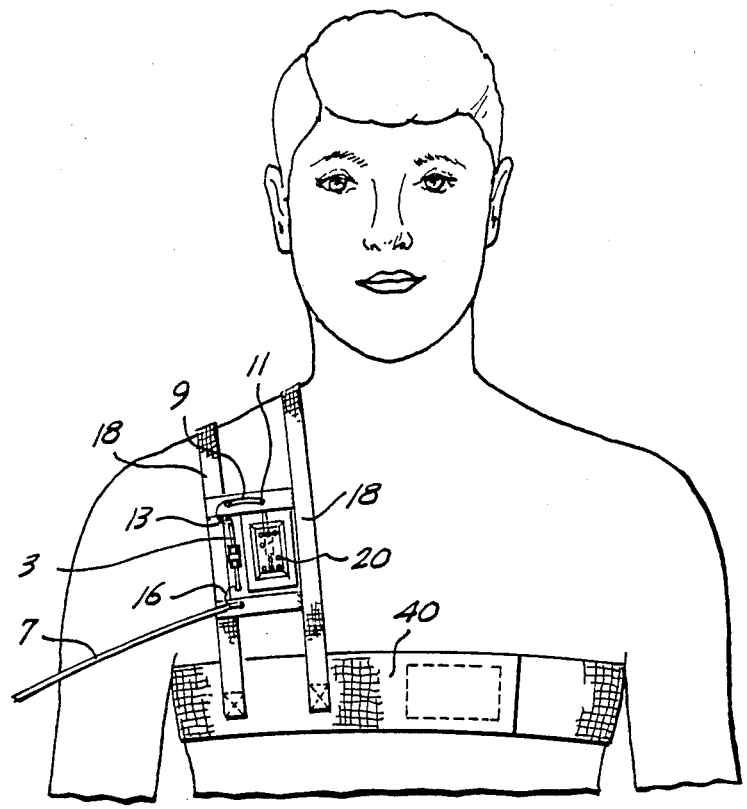
FIG. 7 is a front elevation of the upper body portion of a patient with an IV tube anchor and shield in accordance with FIG. 1 applied over the chest.

FIG. 7 illustrates the assembled combination of frame 9, straps 18 and dome 20 as applied over the chest of a patient. Straps 18 are looped over one of the patient's shoulders and have their opposite end portions secured to a larger chest strap 40 at the front and back of the patient, respectively. Insertion of an IV needle in the chest area may be desired for dialysis, chemotherapy or infant intravenous feeding. As in the previously described embodiments, the puncture area is protected by the dome or shield 20 and the IV tube 3, 7 extends through the frame end slot 11 and under the corner tabs 13 and 16 which are held down by one of the straps 18—such straps preferably having patches or strips of fastening material positioned for mating with complementary patches or strips of fastening materials mounted on the frame 9 to hold the tabs down and secure the frame in position.

I claim:

1. In mechanism for securing an IV tube extending from an IV needle inserted in a patient which mechanism includes an anchor member, means for securing the anchor member to the patient adjacent to the puncture area of the IV needle and means for securing such tube to the anchor member, the improvement comprising the anchor member having a generally U-shaped cut defining an opening, the tube-securing means including a flap normally closing said opening but raisable relative to the remainder of said anchor member for insertion of the IV tube thereunder to retain the IV tube engaged between said flap and the marginal portion of said anchor member adjacent to said cut.

2. In the mechanism defined in claim 1, the anchor member including a sheet material portion having the generally U-shaped cut, such cut being in the form of a narrow slit with substantially circular holes at the opposite ends thereof, the flap being integral with such anchor member portion for swinging substantially along a line extending between said holes for insertion of the IV tube thereunder to fit in said circular holes.

3. In the mechanism defined in claim 1, the flap being integral with the remainder of the anchor member.

4. In the mechanism defined in claim 3, means for biasing the flap toward the remainder of the anchor member after insertion of the IV tube under the flap.

5. In the mechanism defined in claim 4, the biasing means including a strap and means for retaining said strap extending snugly over and engaged against flap.

6. Mechanism for protecting an IV needle inserted on a patient and having an IV tube extending therefrom comprising a continuous frame having a central aperture, means for securing said frame to the patient with said aperture surrounding the puncture area of the IV needle, and means for anchoring the IV tube to said frame, said securing means including an ankle cuff, means for securing said ankle cuff to the lower leg of the patient and means for securing said frame to said ankle cuff over the foot of the patient.

* * * * *

UNITED STATES PATENT AND TRADEMARK OFFICE
CERTIFICATE OF CORRECTION

PATENT NO. : 4,846,807
DATED : July 11, 1989
INVENTOR(S) : Gary J. Safadago

It is certified that error appears in the above-identified patent and that said Letters Patent is hereby corrected as shown below:

Title page, Section 56, the Heitzman patent number should be ...4,574,798...

Column 1, line 5, cancel "858,143." and insert ...858,134,...

Claim 5: column 4, line 43, after "against" insert ...the...

Claim 6: column 4, line 44, cancel "on" and insert ...in...

Signed and Sealed this

Nineteenth Day of June, 1990

*Attest:*

HARRY F. MANBECK, JR.

*Attesting Officer*  *Commissioner of Patents and Trademarks*